United States Patent
Herndon et al.

(10) Patent No.: US 11,590,332 B2
(45) Date of Patent: Feb. 28, 2023

(54) PRECISION MICRONEEDLING DEVICE AND METHODS OF USE

(71) Applicant: Path Scientific, LLC, Carlisle, MA (US)

(72) Inventors: Terry O. Herndon, Carlisle, MA (US); Thiruvallur R. Gowrishankar, Acton, MA (US)

(73) Assignee: Path Scientific, LLC, Carlisle, MA (US)

( * ) Notice: Subject to any disclaimer, the term of this patent is extended or adjusted under 35 U.S.C. 154(b) by 471 days.

(21) Appl. No.: 16/848,036

(22) Filed: Apr. 14, 2020

(65) Prior Publication Data

US 2020/0330737 A1 Oct. 22, 2020

Related U.S. Application Data

(60) Provisional application No. 62/835,021, filed on Apr. 17, 2019.

(51) Int. Cl.
*A61L 31/00* (2006.01)
*A61M 37/00* (2006.01)
*A61B 5/00* (2006.01)
*A61M 5/00* (2006.01)

(52) U.S. Cl.
CPC ....... *A61M 37/0015* (2013.01); *A61B 5/0015* (2013.01); *A61B 5/0024* (2013.01); *A61M 5/00* (2013.01); *A61M 2037/0061* (2013.01); *A61M 2205/0233* (2013.01)

(58) Field of Classification Search
None
See application file for complete search history.

(56) References Cited

U.S. PATENT DOCUMENTS

| | | | |
|---|---|---|---|
| 9,345,487 B2 * | 5/2016 | Herndon | A61B 17/205 |
| 2014/0222003 A1 | 8/2014 | Herndon et al. | |
| 2017/0120002 A1 | 5/2017 | Barak et al. | |
| 2017/0354810 A1 | 12/2017 | O'Brien, III et al. | |
| 2018/0103968 A1 | 4/2018 | Proctor et al. | |

OTHER PUBLICATIONS

PCT International Search Report dated Jul. 2, 2020 from PCT/US2020/028186.
PCT Written Opinion dated Jul. 2, 2020 from PCT/US2020/028186.

* cited by examiner

*Primary Examiner* — Susan T Tran
(74) *Attorney, Agent, or Firm* — Banner & Witcoff, Ltd.

(57) ABSTRACT

Disclosed is a microneedling device and a method for the microneedling of human or animal tissue. The method comprises the following steps; (a) providing a microneedling device having an electrically conductive microneedle and an electrically conducting nosepiece assembly spaced apart from the electrically conductive microneedle and acting as a counter electrode; (b) placing the electrically conductive microneedle and nosepiece assembly into contact with the tissue to be microneedled; (c) measuring the electrical impedance between the microneedle tip and the nosepiece or the current through the microneedle motor; (d) commencing insertion of the microneedle and moving the microneedle toward the tissue surface; (e) starting a step counter when the impedance reduces or the microneedle motor current increases; (f) incrementing the step counter with every step of the vertical drive motor until the step count reaches the prespecified value thereby controlling the depth of the hole microneedled.

14 Claims, 4 Drawing Sheets

PATHFORMER DEVICE-1

| 1 – Plastic Housing | 2 – Motor Coupling | 3 – Vertical Drive Motor (Stepper Motor) |
| --- | --- | --- |
| 4 – Printed Circuit Board | 5 – Top Plate | 6 – Microneedle Motor |
| 7 – Actuator Switch | 8 – Nosepiece | 9 – Microneedle |
| 10 – Stationary Frame | 11 – Moving Carriage | 12 – Guide Pins |
| 13 – Nut Keeper | 14 – LED | 15 – Bottom Plate |
| 16 – Lead Nut | 17 – Lead Screw | 18 – Chuck |
| 19 – Microneedle Motor Plate | 20 – PCB Spacer | 21 – Vertical Drive Motor Plate |
| 22 – Lock Nut | | |

Small prototype with power supply and control unit

FIG. 4

PRECISION MICRONEEDLING DEVICE AND METHODS OF USE

CROSS REFERENCE TO RELATED APPLICATION

This application claims priority from commonly owned U.S. Provisional Application Ser. No. 62/835,021, filed Apr. 17, 2019, the disclosure of which is hereby incorporated herein by reference.

FIELD OF THE INVENTION

Microneedling is currently being used to treat a number of skin disorders. The basic idea is the use of tiny needles to penetrate the skin and induce an inflammatory reaction that promotes healing of any underlying pathology. One use is in cosmetic dermatology where collagen production is initiated by the microneedling procedure. This promotes tightening of skin (i.e., wrinkle removal).

BACKGROUND OF THE INVENTION

There are many microneedling devices on the market, each of which creates epidermal and dermal micro-wounds to stimulate collagen production. A range of fixed needle rollers and electric-powered pen devices with disposable sterile needle tips are available. These devices vary based on needle length, quantity, diameter, configuration, and material. Manual rollers and electric-powered pens are operated by gliding perpendicularly over the skin surface until fine pinpoint bleeding is achieved. Electric pens offer several advantages over roller drum devices including the ability to easily adjust their operating speeds and penetration depths thereby permitting treatment of large surface areas efficiently and at varying needle depths as necessary.

The original instrument used for microneedling is popularly known as a 'dermaroller'. A dermaroller is a simple, hand-held instrument consisting of a handle with a cylinder studded with sterile, fine, stainless steel needles of 0.5-2 mm in length. There are usually 192 needles and they are spaced at regular distances from each other. In order to achieve a uniform depth of penetration, the needles are placed at an inclination of 15 degrees in relation to the surface of the dermaroller. The microneedles are synthesized by reactive-ion etching techniques on silicon or medical-grade stainless steel.

As the therapeutic use of microneedling has been extended beyond scar management, various modifications have occurred since the dermaroller was originally introduced. Home-care dermarollers, with needles less than 0.1 mm in length have been introduced for transdermal delivery of substances like lipopeptides and other anti-ageing products. Another modification includes a miniature version of the dermaroller called a dermastamp, which has needles of 2 mm in length and diameters of 0.12 mm. Dermastamps are used in the treatment of localized scars like varicella scars.

For more background information regarding microneedling devices and methods see the following references, which are hereby incorporated herein by reference:

Alster et al., Microneedling: A Review and Practical Guide, Dermatologic Surgery, pp. 1-8, August 2017.
Majid et al., Microneedling and its Applications in Dermatology, Dermatology, Sep. 15, 2014.
Singh et al., Microneedling: Advances and Widening Horizons, Indian Dermatol Online J., July-August; 7(4): 244-254 (2016).

The precision microneedling device of the present invention is an improved and modified version of a device known as the PathFormer. The PathFormer device is described in U.S. Pat. No. 7,848,799, the disclosure of which is hereby incorporated by reference. See also FDA 510(k) Application No. K052770, approved for the PathFormer device.

Figure 1:
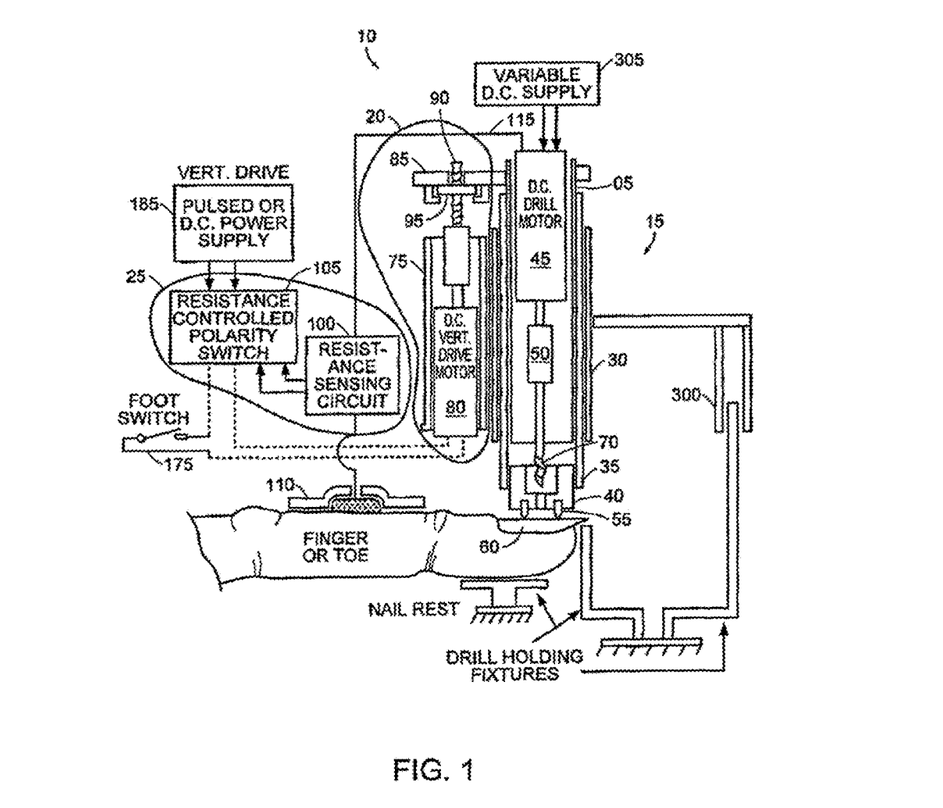
FIG. 1 shows the PathFormer device as described in U.S. Pat. No. 7,848,799. This drawing is labeled as Prior Art.
Figure 2:
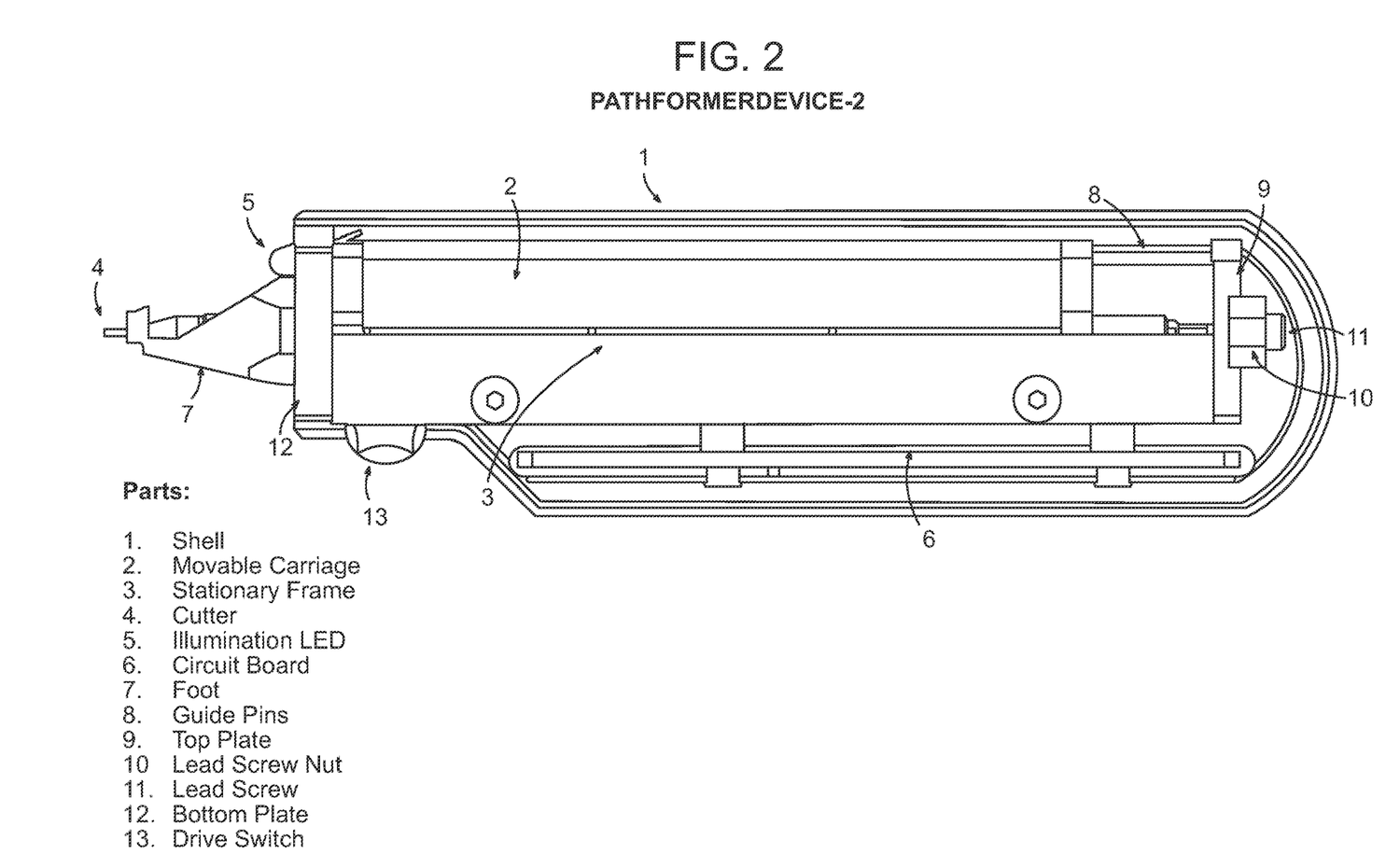
FIG. 2 shows another embodiment of the PathFormer device. This drawing is also labeled as Prior Art. This drawing is taken from the 510(k) Application filed for the PathFormer device.

The PathFormer device is an electrosurgical hand-held device that cuts holes in fingernails and toenails using mesoscissioning technology. It cuts the nail with a micro-cutting tool, using tissue impedance as the feedback mechanism for stopping the cutting action. The PathFormer device is illustrated in FIGS. 1 and 2 herein.

SUMMARY OF THE INVENTION

The present invention makes use of the measured differences in impedance between the microneedle and a counter-electrode on the skin, which is used to characterize the skin surface. The microneedle is then driven into the tissue for a specified depth to effect the desired treatment. One advantage over other microneedling devices and methods is the precise control of depth.

In the present invention, the device does not require different lengths of microneedles. Depth of microneedle insertion into the tissue is controlled, based on the number of steps programmed into the unit, such that precise depth control is provided to the carriage carrying the needle or needle array. An extension of this concept would be using multiple carriages with stepper motors or linear drives to move the individual needles.

The precision microneedling device of the present invention is an improved and modified version of the original PathFormer device used for creating microconduits in nails and/or removing stratum corneum. In some embodiments of the microneedling device of this invention the microneedle serves as one electrode and the nosepiece with an electrically conducting surface that contacts the tissue serves as the counter electrode. In some embodiments, the PathFormer device foot switch is replaced with a hand-operated switch.

In certain embodiments, the PathFormer D.C. vertical drive motor is replaced by a stepper motor. Depth of insertion can be controlled by the number of steps programmed into the control module of the unit.

In certain embodiments, the PathFormer D.C. vertical drive motor is replaced by a linear actuator instead of a stepper motor.

In addition, in certain embodiments, the electronic control circuits of the PathFormer device have been modified to include one or more of the following features:

(1A) start counting the steps of the vertical drive motor and start inserting the microneedle into the tissue once a change in impedance between the microneedle and the electrically conductive nosepiece is sensed (e.g., when the microneedle touches the tissue surface); or (1B) Step counting starts when the current change is detected (e.g., when the microneedle touches the tissue surface);

(2) stop inserting the microneedle and reverse the vertical drive motor when the step count reaches a pre-set count (desired hole depth);

(3) include a current load monitor for added depth control, (4) include a forward motion rate or speed adjustment capability, (5) include a reverse rate or speed adjustment capability, and (6) include an end of reverse motion counter that will stop the reverse motion and reset the system for the next forward cycle.

Another embodiment of the invention provides a method for the precision insertion of the microneedle into human or animal tissue. The method comprises the following steps:

(a) providing a device having an electrically conductive microneedle acting as an electrode and an electrically conducting nosepiece spaced apart from the conductive microneedle and acting as a counter electrode;

(b) placing the electrically conductive microneedle and nosepiece into contact with the tissue to be microneedled;

(c) measuring the electrical impedance between the microneedle and the nosepiece, or measuring the microneedle motor current;

(d) commencing the inserting of the microneedle into the tissue and starting the step counter when the impedance between the microneedle and the nosepiece reaches a pre-set value; or commencing the inserting of the microneedle into the tissue and starting the step counter when the impedance between the microneedle and the nosepiece starts to change;

or commencing the inserting of the microneedle into the tissue and starting the step counter when the microneedle motor current starts to change;

(e) stop the inserting of the microneedle and reversing the vertical drive motor voltage when the step counter reaches a pre-set value—as selected by the device operator based on the requirements of the case; or stop inserting the microneedle when the vertical drive motor current starts to change.

It should be appreciated by those persons having ordinary skill in the arts to which the present invention relates that any of the features described herein in respect of any particular aspect and/or embodiment of the present invention can be combined with one or more of any of the other features of any other aspects and/or embodiments of the present invention described herein, with modifications as appropriate to ensure compatibility of the combinations. Such combinations are considered to be part of the present invention contemplated by this disclosure.

It is to be understood that both the foregoing general description and the following detailed description are exemplary and explanatory only and are not restrictive of the invention as claimed. Other embodiments will be apparent to those skilled in the art from consideration of the specification and practice of the invention disclosed herein.

DETAILED DESCRIPTION OF THE INVENTION

As described above, the present invention is directed to a microneedling device used for inserting one or more microneedles into human or animal tissue, said microneedling device comprising:

(a) a housing that includes a microneedle and an electrically conductive nosepiece assembly to be placed in contact with tissue to be microneedled;

(b) a microneedle moved by an electric motor which is mobile in translation in the housing and wherein the microneedle is electrically conductive and is adapted to be moved into and out of the tissue being microneedled;

(c) a control module electrically connected to the microneedle assembly for controlling the translation of the microneedle in the housing and into and out of the tissue being microneedled;

(d) a sensor, electrically connected to the microneedle assembly and to the control module for detecting a change in an electrical impedance between the microneedle and the surface of the tissue being microneedled when the microneedle is translated to the tissue being microneedled; wherein the sensor, upon detection of a change in the electrical impedance corresponding to a transition between air (no load; high electrical impedance) and tissue surface, sends a signal to the control module to begin incrementing a step counter;

(e) automatically reverse the direction of the vertical drive motor when the step counter reaches a prespecified count, thereby withdrawing the microneedle from the tissue being microneedled, and thereby controlling the depth of the microneedled hole.

In certain embodiments of the microneedling device, the microneedle is moved toward and away from the tissue by a vertical drive motor that may be a stepper motor.

In certain embodiments of the microneedling device, the microneedle is moved toward and away from the tissue by a vertical drive motor that may be a linear actuator.

In certain embodiments of the microneedling device, the device further comprises a replaceable microneedle and nosepiece assembly that are attached to the device to provide a disposable unit. The microneedle dimension (length & diameter) is selected by the operator based on the needs of the patient and the condition being treated. The sizes of the prior art microneedling devices are applicable for use in the device of the present invention.

In certain embodiments of the microneedling device, the microneedle is moved forward and back by a stepping motor, which includes a power supply and settable step counter control. In certain embodiments of the microneedling device, the step counter control starts counting the steps once a pre-set trigger impedance is sensed between the microneedle and the electrically conductive impedance sensing electrode or the nosepiece of the housing.

In certain embodiments of the microneedling device, the device includes a vertical drive motor step counter that can be pre-set to stop the forward motion of the microneedle after reaching the desired count, and thus the desired microneedle depth. In certain embodiments of the microneedling device, the device includes a load (electrical current) monitor for added depth control of the microneedle. In certain embodiments of the microneedling device, the device includes a forward motion rate or speed adjustment capability, for added depth control of the microneedle.

In certain embodiments of the microneedling device, the device includes a reverse rate or speed adjustment capability.

In certain embodiments of the microneedling device, the device includes an end of reverse motion counter that will stop the reverse motion and reset the system for the next forward cycle.

In certain embodiments of the microneedling device, the device is controlled by the control module such that after the initial characterization of the tissue surface, the microneedle, with a foot having no anchor pins, rapidly travels a preselected small number of steps into the tissue and the same number of steps back. The process is repeated at several sites on the tissue by laterally moving the device on the tissue to create a pattern on the tissue surface.

Another embodiment of the invention is directed to a device for inserting a microneedle into human or animal tissue, said microneedling device comprising:

(a) a housing that includes a microneedle assembly and an electrically conductive nosepiece assembly to be placed in contact with tissue to be microneedled;

(b) a microneedle moved by an electric motor which is mobile in translation in the housing and wherein the microneedle is electrically conductive and is adapted to be moved into and out of the tissue being microneedled;

(c) a control module electrically connected to the microneedle assembly for controlling the translation of the microneedle in the housing and into and out of the tissue being microneedled;

(d) a sensor, electrically connected to the microneedle assembly and to the control module for detecting a change in electrical current through the microneedle motor; wherein the sensor, upon detection of a change in the electrical current through the microneedle motor corresponding to a transition between air (no load) and tissue surface, sends a signal to the control module to begin incrementing a step counter;

(e) automatically reverse the direction of the microneedle when the step counter reaches a prespecified count, thereby withdrawing the microneedle from the tissue being microneedled, and thereby controlling the depth of the microneedle insertion; and (f) automatically reverse the direction of the vertical drive motor when the vertical drive motor current starts decreasing thereby withdrawing the microneedle, as described above.

Another embodiment of the invention is a method for conducting the insertion of a microneedle into human or animal tissue comprising the following steps:

(a) providing an embodiment of the precision microneedling device of this invention, the device having an electrically conductive microneedle and an electrically conducting nosepiece assembly spaced from the conductive microneedle, and acting as a counter electrode;

(b) placing the conductive microneedle and nosepiece assembly into contact with the tissue to be microneedled;

(c) commencing the inserting of the microneedle into the tissue to be microneedled;

(d) measuring an electrical impedance between the microneedle tip and the counter electrode to obtain impedance data of the tissue being microneedled;

(e) analyzing the electrical impedance data by a control module and starting the increment of a step counter when the electrical impedance changes; and (f) controlling the depth of inserting the microneedle in the tissue by incrementing the step counter with every step of the motor until a prespecified count is reached.

Another embodiment of the invention is a method for inserting the microneedle into human or animal tissue comprising the following steps:

(a) providing an embodiment of the precision microneedling device of this invention, the device having an electrically conductive microneedle and an electrically conducting nosepiece assembly spaced apart from the conductive microneedle, and acting as a counter electrode;

(b) placing the nosepiece assembly into contact with the tissue to be microneedled;

(c) measuring the electrical impedance between the nosepiece and the conductive microneedle;

(d) thereafter commencing the inserting of the microneedle into the tissue to be microneedled;

(e) measuring the electrical current through the microneedle motor;

(f) analyzing the electrical current data by a control module and starting the increment of a step counter when the microneedle motor current increases; and (g) controlling the depth of inserting the microneedle in the tissue by incrementing the step counter with every step of the motor until a prespecified count is reached.

In certain embodiments of the invention, the nosepiece serves as the counter-electrode for electrical impedance sensing. The impedance between the microneedle and the nosepiece on the tissue surface is continually measured to signal the instant that the microneedle touches the tissue and the high electrical impedance between them drops by orders of magnitude during the insertion of the microneedle. This change in electrical impedance starts the count of the stepper motor that moves the microneedle into the tissue. Once the pre-programmed depth is reached, the microneedle is automatically retracted out and away from the tissue.

In certain embodiments, the device is equipped with a programmable control module that detects when the microneedling device touches the surface of the tissue by sensing the change in electrical impedance between the microneedle and the device nosepiece that rests against the tissue surface. This nosepiece can include small, sharp pins that penetrate the tissue slightly and prevent lateral motion (sliding) on the tissue by the device. The electrical impedance is very high between the microneedle and nosepiece until the microneedle touches the tissue surface, when the electrical impedance drops orders of magnitude due to the high electrical conductivity of the body's natural saline environment present on the patient's tissue.

Array of Openings

While the device of the present invention described above generally makes one opening in tissue, the device can also be modified to make an array of microneedle openings in tissue—thereby treating a larger area of tissue at one time.

One embodiment for making an array of microneedle tissue openings is to drive an array of microneedles and use a change in impedance or change in drive current that is indicative of all the needles touching the skin. For example, the average impedance or current change from all of the needles can be used as a guide for implementing the insertion of the microneedles into the tissue.

Another embodiment for making an array of microneedle tissue openings is to drive the array of microneedles using an array of stepper motors or an array of linear actuators. This method would allow the operator to determine when each needle touches the skin independently.

Precise Depth Function

The depth of the hole being microneedled can be programmed into the control module as a certain number of steps to be taken by a 'stepper' motor that turns a lead screw. The stepper motor is mounted to the moving carriage of the device to which the microneedle motor of the device is attached. The stepper motor turns a lead screw that is threaded through a nut attached to the stationary frame of the device. This moves the moving carriage along guide pins in the stationary frame to which the nosepiece of the device is attached. Thus, the stepper motor turns the lead screw to move the microneedle and microneedle motor toward and away from the microneedling to be microneedled. In certain embodiments, the stepper motor can be mounted on the stationary frame and the nut can be attached to the moving carriage.

The control module can be programmed to send a precise number of electrical pulses to the stepper motor. Each pulse moves the stepper motor a set distance. The operator places the nosepiece against the tissue, presses and holds the actuator switch (or optional foot switch or a nosepiece switch) and the microneedle is moved toward the tissue. When the electrical impedance or current change is detected, the increment of the step counter is started. Having moved a predetermined number of steps, the microneedle is automatically withdrawn from the tissue. The operator has the option of releasing the actuator switch and the microneedle is automatically rapidly withdrawn from the tissue as a 'fail-safe' feature.

In certain embodiments, the microneedle and microneedle motor (electric or air powered) are mounted on a moveable carriage, and positioned by a stepper motor-driven lead screw.

In certain embodiments, an on-board control module measures the electrical impedance and acting in conjunction with the stepper motor, controls the position of the microneedle, its approach speed, its precise position while inserting the microneedle and its withdrawal rate.

Example

Figure 3:
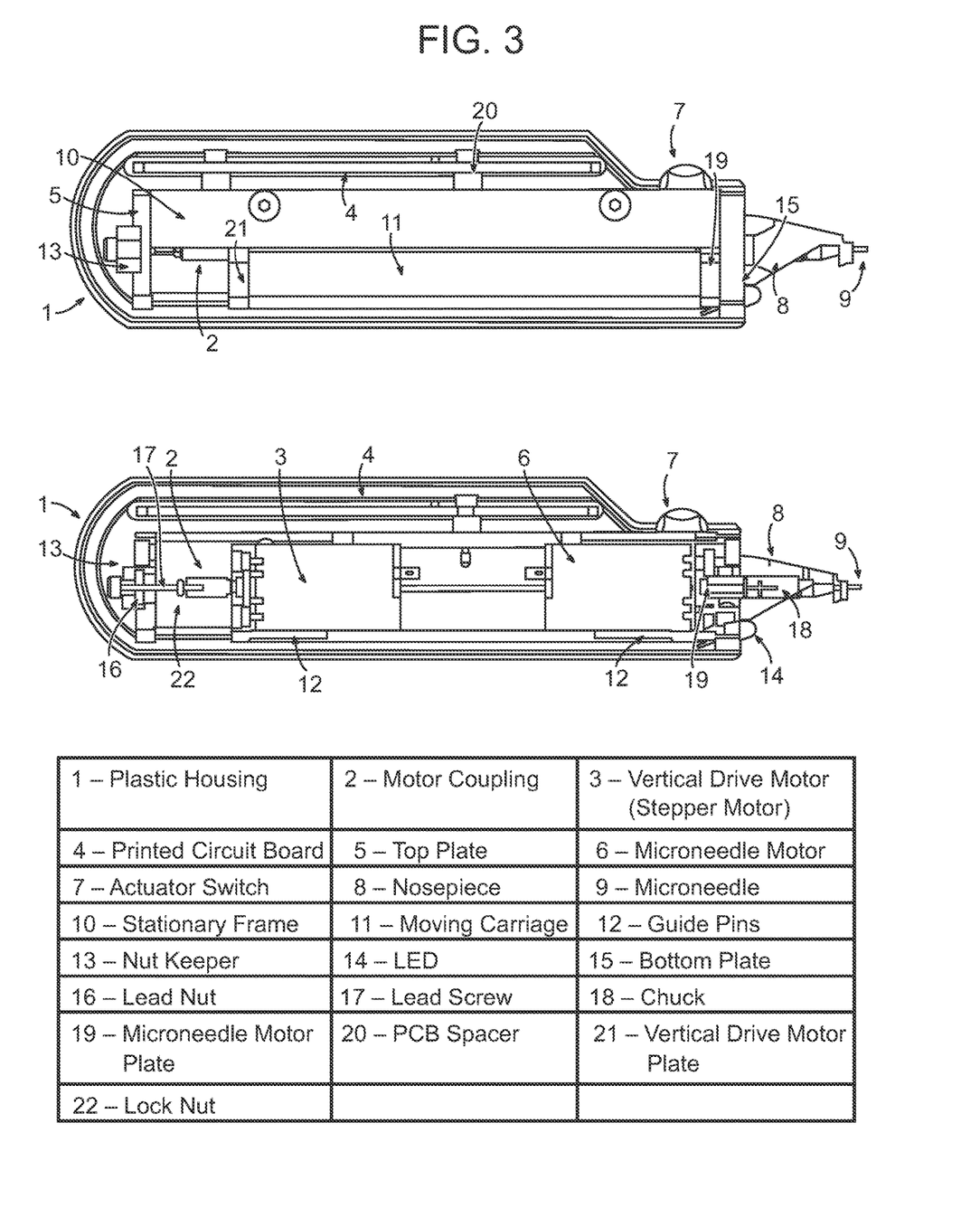
FIG. 3 shows an embodiment of the Precision Microneedling Device of the present invention.

A cross-section of the microneedling device and its components are shown in FIG. 3. The different parts are numbered in the caption. The microneedling device consists of the following main functional elements: a microneedle, foot, a microneedle drive motor and a vertical drive motor. The microneedle drive motor, mounted on a movable chassis, moves the microneedle. The vertical drive motor coupled to a lead screw steps the movable chassis toward/into or away/out of the tissue. The microneedle can be rotated during insertion if desired, but may also be inserted without rotation.

Figure 4:
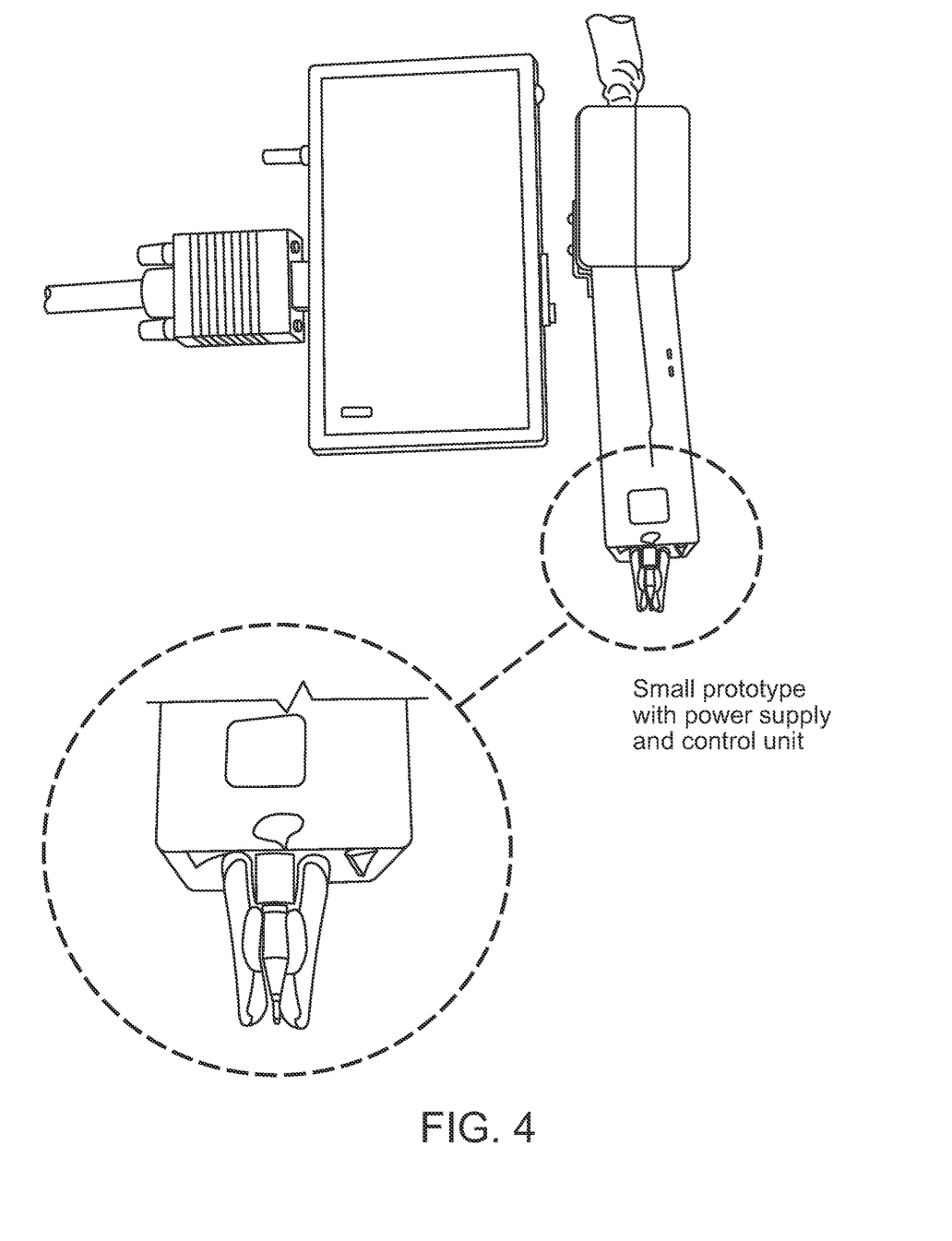
FIG. 4 shows an embodiment of the Precision Microneedling Device of the present invention, with a detailed view of the microneedle and nosepiece parts of the device.

The components of the microneedling device are housed in a plastic outer housing (Parts 1 and 2 in FIG. 3) that is split into fully conforming halves. The hand-actuated switch to operate the device protrudes through an opening in the housing. The cables to the sensing electrodes are connected to the circuit board. The cables to the power supply are connected through an access port toward the back of the housing (FIG. 4).

The microneedling device chassis has two parts: a stationary frame (Part 10 in FIG. 3) and a movable carriage (part 11 in FIG. 3). The two parts are connected to each other through a top plate (Part 5 in FIG. 3) and a bottom plate (Part 15 in FIG. 3) by pairs of guide pins (Part 12) in each plate. The microneedle motor is connected to the end of the movable carriage by screws to its end plate (Part 19). The vertical drive motor is connected to the movable carriage by screws to its end plate (Part 21).

The microneedle and vertical motor end plates have pairs of holes in them, the moveable carriage has sufficiently long, oversized holes that match the end plate holes. The holes in the plate (part 5) and bottom plate (plate 15) have guide pins pressed into them. These guide pins pass through the clearance holes in the microneedle motor end plate (Part 19) and the vertical drive end plate (Part 21) and further through the holes in the movable carriage. Thus the assembled movable carriage can slide on the guide pins in the stationary frame. The lead screw (Part 17) that passes through a nut keeper (Part 13) holds the lead screw nut (Part 16). The lead screw is connected to the vertical motor by a coupling element (Part 2).

The control module electronics, that control the two motors, are contained in two circuit boards. One circuit board (Part 4) that is fixed to the stationary frame contains an onboard control module. The circuitry on this board measures the impedance between the microneedle and the nosepiece. It also sends the motion direction and on/off signals to the two motors (Part 6 and Part 3). The second circuit board is located inside the external power supply unit (FIG. 4). This board has a stepper motor controller (PRECIstep, Faulhaber) that controls the vertical drive motor. In addition, the power supply unit has a variable voltage regulator that powers the microneedle motor and the first circuit board. Conductors from the circuit board and power supply unit connect to the motors, microneedle and the nosepiece.

The microneedling device with its associated electronics is run by a rechargeable battery housed in the power supply unit. A white 3 mm LED (RL3-W6045, commercially available at superbridgeleds.com) may be used to illuminate the microneedle area. The LED (light emitting diode, Part 14 in FIG. 3) is powered by the control circuit. The microneedle is held in place by a chuck, with three equally spaced slits, which is attached to the spindle of the microneedle motor. The nosepiece (Part 9 in FIG. 3), made of or coated with an electrically conducting material, is fixed to the device with a lock-in screw. This part encloses, but does not physically contact the microneedle.

The motor that drives the microneedle is a 6V DC motor (1524T006S, Faulhaber). It is operated at 10,000 rpm using a 6 V pulsed input (50% duty cycle). The vertical drive motor is a two-phase 6V stepper motor (ADM0620-2R-ww-ee; Faulhaber) that is attached to the lead screw and the movable chassis. The lead screw moves in a nut fixed to the stationary frame thus moving the microneedle towards or away from the cutting surface.

The onboard control module regulates the direction and the pulsing signals of the stepper motor controller. The onboard control module also keeps count of the number of steps taken by the vertical drive motor. The impedance between the microneedle and the nosepiece is measured with a 2 kHz, 0.1 V square wave input. The impedance is compared with a pre-set trigger impedance. The difference signal is amplified by a two-stage amplifier, the output of which is used to start/stop the microneedle motor and start/stop/reverse the vertical drive motor.

The microneedling device is assembled, from the parts listed in FIG. 3, as described below. Insert a pair of longer guide pins (Part 12) through the top plate (Part 5) with the tapered ends into the holes and gently press each in. Place the lead nut (Part 16) in the groove of the top plate (Part 5) and place the nut keeper (Part 13) on top in the groove and put in the two longer screws. Crimp the screws' bottom to avoid the screws loosening. Apply some epoxy on the motor shaft and push the motor coupling (Part 2) on the motor shaft. Let it cure. Fix the vertical drive motor plate (Part 21) on to the vertical drive (stepper) motor (Part 3) and fix the microneedle motor plate (Part 19) to the microneedle motor (Part 6) using small screws. Insert the lead screw (Part 17) through the top plate (Part 5). Insert the lock nut (Part 22) half way into the lead screw (Part 17).

Connect the vertical drive motor plate (Part 21) to the vertical drive (stepper) motor with screws. Add some glue into the motor coupling on the lead screw side. Immediately screw the lead screw as far as possible into the motor coupling. Bring down the lock nut to be flush with the motor coupling. Add more glue around the nut. Tighten firmly against the motor coupling. Let it cure. Put some glue on the microneedle motor shaft and insert the shaft (Part 18) into the microneedle chuck and let it cure.

Insert shorter guide pins into the bottom plate and press each it in to be flush with the plate surface. Scratch the surface of the microneedle motor close to the terminal end with a knife and expose a 1 $mm^2$ area of the surface. Apply a tiny amount of solder on the exposed area, and solder the impedance-sensing lead from the circuit board to the motor body. Cover the microneedle motor body with an electrical tape.

Attach the microneedle motor plate of the microneedle motor to the other end of the moving carriage. Insert the guide pins of the bottom plate into the moving carriage. Connect wires to the two motor leads. Run the wires through the opening in the stationary frame. Solder the wires to the printed circuit board (PCB, Part 4). Ensure proper polarity of the motor. Screw the stationary frame to the top plate and the bottom plate (four screws). Connect the PCB to the stationary frame with two long screws and spacers (Part 20). Clip the two leads of the white LED (Part 14) and solder two wires and connect the wires to power and ground through a series resistor (220 ohms). Attach two leads from the switch on the circuit board to the actuator switch (Part 7). Tape the switch on to the stationary frame with adhesive. Place the rubber cover over the actuator switch (Part 7). Attach the power cable to power connector on the PCB. Place the two halves of the housing (Part 1) around the moving carriage and stationary frame and attach them using the flat screws.

For further information, see U.S. Pat. No. 9,345,487, the disclosure of which is hereby incorporated herein by reference.

As used herein, the singular forms "a", "an" and "the" include plural unless the context clearly dictates otherwise. Moreover, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

It should be understood that the foregoing description is only illustrative of the present invention. Various alternatives and modifications can be devised by those skilled in the art without departing from the invention. Accordingly, the present invention is intended to embrace all such alternatives, modifications and variances that fall within the scope of the appended claims.

What is claimed is:

1. A method of inserting a microneedle into human or animal tissue comprising the steps of:
   providing a microneedling device, said device comprising:
      (a) a housing that includes a microneedle assembly and an electrically conductive nosepiece assembly to be placed in contact with tissue to be microneedled;
      (b) a microneedle moved by an electric motor which is mobile in translation in the housing and wherein the microneedle is electrically conductive and is adapted to be moved into and out of the tissue being microneedled;
      (c) a control module electrically connected to the microneedle assembly for controlling the translation of the microneedle in the housing and into and out of the tissue being microneedled;
      (d) a sensor, electrically connected to the microneedle assembly and to the control module for detecting a change in an electrical impedance between the microneedle and the surface of the tissue being microneedled; wherein the sensor, upon detection of a change in the electrical impedance corresponding to a transition between air (no load; high electrical impedance) and tissue surface, sends a signal to the control module to begin incrementing a step counter;
      (e) automatically reverse the direction of the vertical drive motor when the step counter reaches a pre-specified count, thereby withdrawing the microneedle from the tissue being microneedled, and thereby controlling the depth of the microneedled hole;
   and inserting the microneedle into the tissue with said microneedling device, wherein the microneedle is moved toward and away from the microneedling by a vertical drive motor that comprises a stepper motor.

2. The method of claim 1, wherein the stepper motor further includes a stepping power supply and settable counter control.

3. The method of claim 2, wherein the counter control starts counting the steps once a pre-set trigger impedance is sensed between the microneedle and the electrically conductive impedance sensing electrode or the nosepiece of the housing.

4. The method of claim 1, further including a vertical drive motor step counter that can be pre-set to stop the forward motion of the microneedle after reaching the desired count, and thus the desired microneedle depth.

5. The method of claim 1, wherein the device further comprises a replaceable microneedle and nosepiece assembly that are attached to the device to provide a disposable unit.

6. The method of claim 1, further comprising an electrical current load monitor for added depth control of the microneedle.

7. The method of claim 1, further comprising a forward motion rate or speed adjustment capability, for added depth control of the microneedle.

8. The method of claim 1, further comprising including a reverse rate or speed adjustment capability.

9. The method of claim 1, further comprising an end of reverse motion counter that will stop the reverse motion and reset the system for the next forward cycle.

10. The method of claim 1, wherein an array of microneedles is employed in the microneedle assembly, using a single motor for the array and using the average impedance/current to identify the tissue surface.

11. The method of claim 1, wherein an array of microneedles is employed in the microneedle assembly, using an array of stepper motors or linear actuators that drive individual needles in the array.

12. A method for conducting microneedling of human or animal tissue comprising the following steps:

provQuestioniding a microneedling device as defined in claim 1, having an electrically conductive microneedle and an electrically conducting nosepiece assembly spaced from the conductive microneedle, and acting as a counter electrode;

placing the electrically conductive microneedle and nosepiece assembly into contact with the tissue to be microneedled;

commencing the insertion of the microneedle into the tissue to be microneedled;

measuring an electrical impedance between the microneedle tip and the counter electrode to obtain impedance data of the tissue being microneedled;

analyzing the electrical impedance data by a control module and starting the increment of a step counter when the electrical impedance decreases; and controlling the depth of insertion of the microneedle in the tissue by incrementing the step counter with every step of the motor until a prespecified count is reached.

13. The method of claim 12, wherein an array of microneedles is employed in the microneedle assembly, using a single motor for the array and using the average impedance/current to identify the tissue surface.

14. The method of claim 12, wherein an array of microneedles is employed in the microneedle assembly, using an array of stepper motors or linear actuators that drive individual needles in the array.

* * * * *